US008235042B2

(12) United States Patent
Newman, Jr.

(10) Patent No.: US 8,235,042 B2
(45) Date of Patent: Aug. 7, 2012

(54) EXHALATORY PRESSURE DEVICE AND SYSTEM THEREOF

(75) Inventor: Lionel Newman, Jr., Los Angeles, CA (US)

(73) Assignee: Wet Nose Technologies, LLC, Los Angeles, CA (US)

( * ) Notice: Subject to any disclaimer, the term of this patent is extended or adjusted under 35 U.S.C. 154(b) by 1345 days.

(21) Appl. No.: 11/849,259

(22) Filed: Aug. 31, 2007

(65) Prior Publication Data
US 2009/0056719 A1 Mar. 5, 2009

(51) Int. Cl.
*A61M 16/00* (2006.01)

(52) U.S. Cl. ......... 128/204.18; 128/200.24; 128/204.15; 128/205.12; 128/205.27; 128/204.16

(58) Field of Classification Search ............. 128/200.29, 128/202.27, 204.16, 204.18, 205.12, 205.23, 128/203.27, 205.28, 206.11, 207.18
See application file for complete search history.

(56) References Cited

U.S. PATENT DOCUMENTS

| | | | |
|---|---|---|---|
| 1,304,327 A | 5/1919 | Klay | |
| 1,314,855 A | 9/1919 | Carpenter | |
| 1,889,425 A | 11/1932 | Sorensen | |
| 2,088,720 A | 8/1937 | Poliniak | |
| 2,295,528 A | 9/1942 | Cutter et al. | |
| 2,328,995 A | 9/1943 | Olds | |
| 2,375,711 A | 5/1945 | Vondrak | |
| 2,422,702 A | 6/1947 | Rodanet | |
| 2,449,497 A | 9/1948 | McLeod | |
| 2,812,765 A | 11/1957 | Tofflemire | |
| 3,065,749 A | 11/1962 | Brass | |
| 3,710,780 A | 1/1973 | Milch | |
| 3,749,090 A | 7/1973 | Stewart | |
| 3,804,089 A | 4/1974 | Bridgman | |
| 3,827,433 A | 8/1974 | Shannon | |
| 3,908,704 A * | 9/1975 | Clement et al. | 138/121 |
| 3,949,749 A | 4/1976 | Stewart | |
| 3,972,326 A | 8/1976 | Brawn | |
| 4,080,989 A * | 3/1978 | Chapelsky et al. | 137/588 |
| 4,215,476 A | 8/1980 | Armstrong | |
| 4,299,221 A | 11/1981 | Phillips et al. | |
| 4,459,983 A | 7/1984 | Beyreuther et al. | |
| 4,464,316 A | 8/1984 | Michaels | |
| 4,468,216 A | 8/1984 | Muto | |
| 4,617,013 A | 10/1986 | Betz | |

(Continued)

FOREIGN PATENT DOCUMENTS
EP 0979660 A 2/2000
(Continued)

OTHER PUBLICATIONS

OA dated May 28, 2010 for U.S. Appl. No. 11/849,268, 39 pages.

(Continued)

*Primary Examiner* — Clinton T Ostrup
(74) *Attorney, Agent, or Firm* — Turocy & Watson, LLP

(57) ABSTRACT

An apparatus for providing pressure into which a patient must exhale is provided. The canister has a canister axis and is disposed to hold liquid. The canister also has indicia of pressure on the canister. The apparatus also includes a substantially rigid lid disposed to substantially cover a mouth of the canister and having a first inlet through the lid. The apparatus also includes an adapter in the first inlet. The apparatus also includes a conduit being retained by the adapter such that the conduit is substantially immovable relative to the canister axis.

20 Claims, 4 Drawing Sheets

U.S. PATENT DOCUMENTS

| | | | |
|---|---|---|---|
| 4,634,420 | A | 1/1987 | Spinosa et al. |
| 4,857,047 | A | 8/1989 | Amoils |
| 5,167,622 | A | 12/1992 | Muto |
| 5,255,675 | A | 10/1993 | Kolobow |
| 5,263,934 | A | 11/1993 | Haak |
| 5,269,296 | A | 12/1993 | Landis |
| D358,475 | S | 5/1995 | Choksi et al. |
| 5,477,852 | A | 12/1995 | Landis et al. |
| 5,557,049 | A | 9/1996 | Ratner |
| 5,575,774 | A | 11/1996 | Chen |
| 5,626,565 | A | 5/1997 | Landis et al. |
| 5,653,231 | A | 8/1997 | Bell |
| 5,687,715 | A | 11/1997 | Landis et al. |
| 5,730,727 | A | 3/1998 | Russo |
| 5,803,310 | A * | 9/1998 | Soon .................................. 222/1 |
| D410,021 | S | 5/1999 | Heyman et al. |
| 5,899,878 | A | 5/1999 | Glassman |
| 6,041,777 | A | 3/2000 | Faithfull et al. |
| 6,045,516 | A | 4/2000 | Phelan |
| 6,050,263 | A | 4/2000 | Choksi et al. |
| 6,149,622 | A | 11/2000 | Marie |
| D439,973 | S | 4/2001 | Choksi |
| 6,284,222 | B1 * | 9/2001 | Driehuys ....................... 424/9.3 |
| D449,378 | S | 10/2001 | Rogone et al. |
| 6,494,203 | B1 | 12/2002 | Palmer |
| 6,520,021 | B1 * | 2/2003 | Wixey et al. ..................... 73/714 |
| D474,269 | S | 5/2003 | Choksi et al. |
| 6,576,191 | B1 | 6/2003 | Myrick et al. |
| 6,770,050 | B2 | 8/2004 | Epstein |
| 6,795,722 | B2 | 9/2004 | Sheraton et al. |
| 6,805,120 | B1 | 10/2004 | Jeffrey et al. |
| 6,805,129 | B1 | 10/2004 | Pless et al. |
| D506,547 | S | 6/2005 | Cruz et al. |
| 6,958,050 | B1 | 10/2005 | Choski et al. |
| 7,066,917 | B2 | 6/2006 | Talamonti |
| 7,077,154 | B2 | 7/2006 | Jacobs et al. |
| 7,185,681 | B2 | 3/2007 | Romano |
| D590,056 | S | 4/2009 | McCrary et al. |
| 7,601,001 | B1 | 10/2009 | McCrary et al. |
| 2001/0044599 | A1 | 11/2001 | Lo |
| 2002/0108614 | A1 | 8/2002 | Schultz |
| 2003/0047185 | A1 | 3/2003 | Olsen et al. |
| 2003/0065263 | A1 | 4/2003 | Hare et al. |
| 2003/0069553 | A1 | 4/2003 | Talamonti |
| 2004/0065330 | A1 | 4/2004 | Landis |
| 2004/0118733 | A1 * | 6/2004 | Pauli .......................... 206/459.5 |
| 2004/0244804 | A1 | 12/2004 | Olsen et al. |
| 2005/0049547 | A1 | 3/2005 | Anspach et al. |
| 2005/0072470 | A1 * | 4/2005 | Jacobs et al. ............... 137/251.1 |
| 2005/0150505 | A1 | 7/2005 | Burrow et al. |
| 2005/0182353 | A1 | 8/2005 | Schmidberger et al. |
| 2005/0256462 | A1 | 11/2005 | Underwood |
| 2005/0277898 | A1 | 12/2005 | Dimalanta et al. |
| 2006/0079832 | A1 | 4/2006 | Akahoshi |
| 2006/0229632 | A1 | 10/2006 | Madden et al. |
| 2007/0078378 | A1 | 4/2007 | Kao et al. |
| 2007/0107737 | A1 | 5/2007 | Landis et al. |
| 2007/0175473 | A1 | 8/2007 | Lewis et al. |
| 2007/0191783 | A1 | 8/2007 | Shaw et al. |

FOREIGN PATENT DOCUMENTS

| | | |
|---|---|---|
| EP | 1084727 | 4/2006 |
| WO | 98/58694 A | 12/1998 |
| WO | 01/64272 A | 9/2001 |
| WO | 2004/033007 A1 | 4/2004 |
| WO | WO 2005056091 A1 * | 6/2005 |
| WO | 2009/029702 A1 | 3/2009 |

OTHER PUBLICATIONS

OA dated Apr. 6, 2009 for U.S. Appl. No. 11/849,268, 9 pages.
International Search Report mailed Nov. 6, 2008 for International Application No. PCT/US2008/074748, 2 pages.
International Search Report mailed Nov. 6, 2008 for International Application No. PCT/US2008/074574, 2 pages.
Frischer, et al. Eosinophil-derived proteins in nasal lavage fluid of neonates of allergic parents and the development of respiratory symptoms during the first 6 months of life. Allergy 2000: 55: 773-777, ISSN 0105-4538. http://onlinelibrary.wiley.com/doi/10.1034/j.1398-9995.2000.00773.x/pdf. Last accessed Oct. 6, 2010, 5 pages.
Waisman. Non-Traumatic Nasopharyngeal Suction in Premature Newborn Infants with Upper Airway Obstruction from Secretions Following Nasal CPAP. J Pediatr 2006;149:279. http://download.journals.elsevierhealth.com/pdfs/journals/0022-3476/PIIS002234760600148X.pdf. Last accessed Oct. 6, 2010, 1 page.
Okada, et al. Pressure-Controlled Dual Irrigation-Suction System for Microneurosurgery: Technical Note. www.neurosurgery-online.com, E625, vol. 65, No. 3, Sep. 2009. http://pt.wkhealth.com/pt/re/merck/pdfhandler.00006123-200909000-00032.pdf;
jsessionid=MsvLyq9Y7c928drTcGsSkYzDJy61CfX4zbyC66q6kcxL5GhdRLKy!1137524313!181195628!8091!-1. Last accessed Oct. 6, 2010, 4 pages.
Vain, et al. Oropharyngeal and nasopharyngeal suctioning of meconium-stained neonates before delivery of their shoulders: multicenter, randomized controlled trial (Abstract), The American College of Obstetricians and Gynecologists, vol. 104, No. 5, Part 1, Nov. 2004.
Garzon, et al. Management of Respiratory Syncytial Virus With Lower Respiratory Tract Infection in Infants and Children. AACN Clinical Issues, vol. 13, No. 3, Aug. 2002, pp. 421-430.
Balfour-Lynn, et al. Nasal IgA response in wheezy infants. Archives of Disease in Childhood 1993; 68: 472-476. Last accessed Oct. 18, 2010, 5 pages.
Celik, et al. A Current Conflict: Use of Isotonic Sodium Chloride Solution on Endotracheal Suctioning in Critically Ill Patients. Dimens Crit Care Nurs. 2006;25(1):11/14. http://www.nursingcenter.com/pdf.asp?AID=630764. Last accessed Oct. 18, 2010, 4 pages.
Stokowski (Section Editor). Endotracheal Suctioning Increases Cerebral Blood Flow in the Very Low Birth-Weight Infant, Advances in Neonatal Care: Apr. 2008—vol. 8—Issue 2—pp. 75-77. doi: 10.1097/01. ANC.0000317254.30460.5d, Noteworthy Professional News, downloaded Mar 24, 2008, 3 pages.
Virolainen, et al. New Method to Assess Dilution of Secretions for Immunological and Microbiological Assays. Journal of Clinical Microbiology, May 1993, p. 1382-1384, vol. 31, No. 5. http://jcm.asm.org/cgi/reprint/31/5/1382. Last accessed Oct. 19, 2010, 3 pages.
Heikkinen, et al. Quantification of Cytokines and Inflammatory Mediators in Samples of Nasopharyngeal Secretions with Unknown Dilution. Pediatric Research: Feb. 1999—vol. 45—Issue 2—pp. 230-234. http://journals.lww.com/pedresearch/Fulltext/1999/02000/Quantification_of_Cytokines_and_Inflammatory.12.aspx#. Last accessed Oct. 19, 2010, 9 pages.
Foglia, et al. Ventilator-Associated Pneumonia in Neonatal and Pediatric Intensive Care Unit Patients. Clinical Microbiology Reviews, vol. 20, No. 3, Jul. 2007, p. 409-425. http://cmr.asm.org/cgi/reprint/20/3/409.pdf. Last accessed Oct. 19, 2010, 17 pages.
Kaiser, et al. Tracheal suctioning is associated with prolonged disturbances of cerebral hemodynamics in very low birth weight infants. Journal of Perinatology (2008) 28, 34-41, published online, Oct. 25, 2007. http://www.umanitoba.ca/faculties/medicine/units/pediatrics/sections/neonatology/media/Oct20-08.pdf. Last accessed Oct. 19, 2010, 8 pages.
Folk. Guide to Capillary Heelstick Blood Sampling in Infants. Advances in Neonatal Care • vol. 7, No. 4 • pp. 171-178. http://www.nursingcenter.com/pdf.asp?AID=735611. Last accessed Oct. 19, 2010, 8 pages.
Lasocki, et al. Open and Closed-circuit Endotracheal Suctioning in Acute Lung Injury: Efficiency and Effects on Gas Exchange. Anesthesiology: Jan. 2006—vol. 104—Issue 1—pp. 39-47, Clinical Investigations. http://journals.lww.com/anesthesiology/Fulltext/2006/01000/Open_and_Closed_circuit_Endotracheal_Suctioning_in.8.aspx. Last accessed Oct. 19, 2010, 9 pages.
Lanter. Clinical Research and the Development of New Devices: Considerations for Nurses. Dimensions of Critical Care Nursing: May/Jun. 2007—vol. 26—Issue 3—pp. 117-120. http://journals.lww.com/dccnjournal/Fulltext/2007/05000/Clinical_Research_and_the_Development_of_New.7.aspx. Last accessed Oct. 19, 2010, 4 pages.
National Nosocomial Infections Surveillance (NNIS) System Report, data summary from Jan. 1992 through Jun. 2004, issued Oct.

2004. http://www.cdc.gov/ncidod/dhqp/pdf/nnis/2004NNISreport.pdf. Last accessed Oct. 19, 2010, 16 pages.

Ingram, et al. Eosinophil Cationic Protein in Serum and Nasal Washes from Wheezing Infants and Children. Journal of Pediatrics, vol. 127, issue 4, Oct. 1995. Retrieved from the internet on Nov. 10, 2010, 11 pages.

Heikkenen, et al. Free Secretory Component as a Standardization Protein for Nasopharyngeal Specimens from Children with Upper Upper Respiratory Tract Infection. Acta Paediatr 88: 150-153, 1999.

Bonner, et al. The Nursing Care of the Infant Receiving Bubble CPAP Therapy. Advances in Neonatal Care • vol. 8, No. 2 • pp. 78-95. Last accessed Nov. 13, 2010, 18 pages.

Klimek, et al. Norm Values for Eosinophil Cationic Protein in Nasal Secretions: Influence of Specimen Collection. Clinical and Experimental Allergy, 1999, vol. 29, pp. 367-374.

Norris, et al. Nursing Procedures and Alterations in Transcutaneous Oxygen Tension in Premature Infants. Nursing Research, vol. 31, No. 6, Nov./Dec. 1982, pp. 330-336.

Samolinski, et al. Changes in Nasal Cavity Dimensions in Children and Adults by Gender and Age. Laryngoscope, 117:1429-1433, Aug. 2007, The American Laryngological, Rhinological and Otological Society, Inc.

Weinstein, et al. Recommendations of the Panel on Cost-Effectiveness in Health and Medicine. JAMA, Oct. 16, 1996—vol. 276, No. 15, 6 pages.

Fisher & Paykel Healthcare Product Catalog copyright 2004, 16 pages.

Fisher & Paykel Healthcare Annual Report 2002, 32 pages.

Petry, Fisher & Paykel 510(k) Summary of Safety and Effectiveness Information, 6 pages, Apr. 3, 2003.

http://www.fphcare.com/rsc.html, last accessed Apr. 26, 2010, 1 page.

http://www.fphcare.com/rsc/infant-care/resuscitation.html, last accessed Apr. 26, 2010, 1 page.

http://www.fphcare.com/rsc/infant-care/non-invasive-ventilation.html, last accessed Apr. 26, 2010, 1 page.

http://www.fphcare.com/rsc/rac-clinical-and-applications/infant-ca/why-bubble-cpap-is-vital.html, last accessed Apr. 26, 2010, 2 pages.

http://www.fphcare.com/product-overview/chambers/humidification-chambers/mr290-autofeed.html, last accessed Apr. 26, 2010, 1 page.

http://www.fphcare.com/product-overview/chambers/humidification-chambers/mr210-mr250-chamber.html, last accessed Apr. 26, 2010, 1 page.

http://www.fphcare.com/product-overview/chambers/humidification-chambers/mr225-manual-feed.html, last accessed Apr. 26, 2010, 1 page.

http://www.fphcare.com/osa/cpap-solutions/cpap/sleepstyle-200.html, last accessed Apr. 26, 2010, 2 pages.

http://www.fphcare.com/osa/cpap-solutions/cpap/sleepstyle-240.html, last accessed Apr. 26, 2010, 2 pages.

http://www.fphcare.com/osa/cpap-solutions/cpap/sleepstyle-600.html, last accessed Apr. 26, 2010, 2 pages.

http://www.fphcare.com/osa/cpap-solutions/autocpap/sleepstyle-250.html, last accessed Apr. 26, 2010, 2 pages.

Babi.Plus™ Bubble PAP Valve 0-10 cm H20, Safe, accurate method to deliver CPAP therapy in neonatal critical care environments, 2010, 1 page.

B&B Medical Technologies, Babi.Plus™ Bubble PAP Valve 0-10 cm H2O, 2005, 2 pages.

B&B Medical Technologies, Babi.Plus™ Bubble PAP Valve 0-10 cm H2O gives clinicians a safe, accurate, convenient method to deliver CPAP therapy for neonates and premature infants, 1 page, Mar. 19, 2010.

Airways Development LLC, Waterseal Canister & Accessories, Aug. 2004, 1 page.

A Plus Medical 510(k) Summary, 5 pages, May 20, 2009.

Presentation Jul. 2007, 16 pages.

http://www.airwaysdevelopment.com/product.asp, last accessed Apr. 28, 2010, 1 page.

OA dated Sep. 29, 2009 for U.S. Appl. No. 11/849,268, 19 pages.

International Search Report mailed Nov. 2, 2004 for International Application No. PCT/IB2003/04419, 2 pages.

OA dated Jan. 13, 2010 for U.S. Appl. No. 11/849,268, 34 pages.

Written Opinion of the International Searching Authority mailed Nov. 6, 2008 for PCT Application No. PCT/US2008/074574, 35 pages.

* cited by examiner

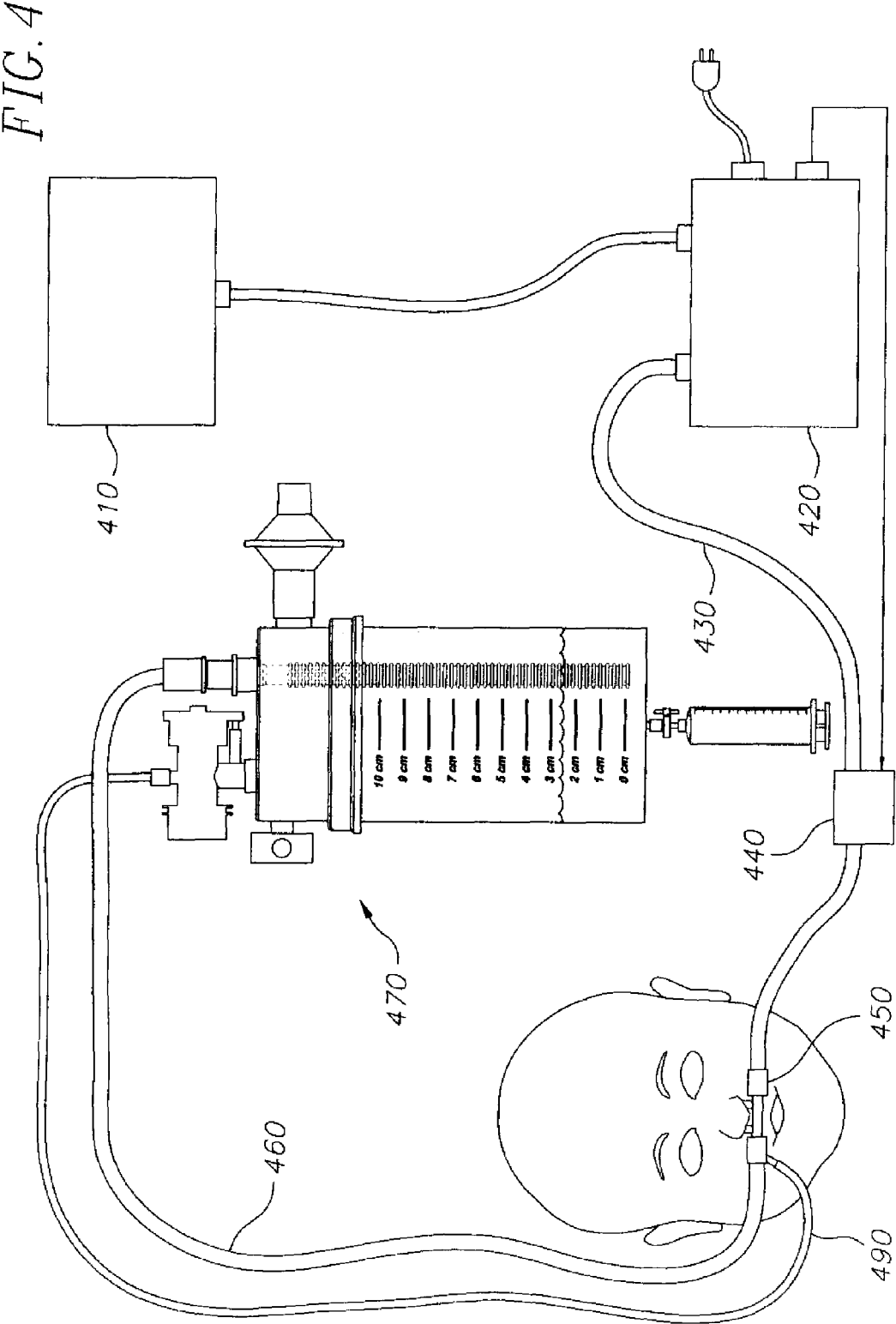

EXHALATORY PRESSURE DEVICE AND SYSTEM THEREOF

FIELD OF THE INVENTION

The present invention relates to bubble nasal continuous positive airway pressure ("BNCPAP") systems and, in particular, to an apparatus for providing exhalatory pressure in BNCPAP systems.

BACKGROUND

BNCPAP systems are used to treat patients such as babies, infants and children having difficulty breathing on their own. In typical BNCPAP systems, patient's exhale into a column of water, thereby creating bubbles. Nasal prongs are placed in the patient's nose. By providing a continuous flow of gas across the patient's nostrils, pressure is increased in the patient's airway. This increase in airway pressure aids the patient in breathing.

Conventional BNCPAP systems include a pressure device designed to contain liquid to provide exhalatory pressure into which a patient must breathe. The patient exhales into a conduit that extends into the liquid of the pressure device. The quantity of the pressure into which the patient must exhale depends on the depth of the conduit in the liquid and the amount of liquid in the device. Accordingly, movable conduits that shift may result in an undesirable and potentially dangerous shift in pressure. Conventional pressure devices include a canister having a very flexible lid with an aperture formed through the lid into which the conduit is positioned. These devices disadvantageously allow the aforementioned movement and corresponding shift in pressure. Accordingly, it is desirable to have a BNCPAP pressure device disposed to provide a substantially stable exhalatory pressure into which a patient must exhale.

Additionally, the pressure device of the BNCPAP system may be filled with any number of liquids, including those that yield an odorous and undesirable scent. Conventional devices merely allow the transmission of the odor into the patient's room where the odor is disruptive to caregivers and patients alike. Additionally, when the liquid is acetic acid, inhalation may increase the risk of mucous membrane injury associated with inhalation of acetic acid vapors. Accordingly, it is desirable to have a pressure device disposed to provide air filtering.

Further, conventional BNCPAP systems provide proximal airway pressure monitoring of nasal continuous positive airway pressure using a non-disposable manometer. Such non-disposable devices can be disadvantageously expensive resulting in an aversion by medical organizations to the use of the devices, which poses risks to the patient. Accordingly, it is desirable to have a non-disposable pressure gauge for measuring proximal airway pressure of the patient.

Further, pressure devices in BNCPAP systems are conventionally placed in locations that make use of the device awkward. Further, depending on the available infrastructure in a room in which a patient is being treated, there may be no suitable mechanism for support of the pressure device. Accordingly, it is desirable to have a pressure device having a built-in mechanism for coupling the pressure device to a range of structures in the room.

Finally, conventional pressure devices in BNCPAP systems require removal of the lid and disconnection of one or more structures attached to the pressure device to fill the device and/or adjust the level of liquid in the device. Accordingly, it is desirable to have a pressure device disposed to provide convenient filling of liquid and adjustment of the level of liquid in the device.

SUMMARY OF THE INVENTION

In one or more embodiments of the present invention, an apparatus for providing pressure into which a patient must exhale is provided. The apparatus includes a canister having a canister axis and being disposed to hold liquid. The canister also has indicia of pressure on the canister. The apparatus also includes a substantially rigid lid disposed to substantially cover a mouth of the canister and having a first inlet through the lid. The apparatus further includes an adapter in the first inlet. The apparatus further includes a conduit being retained by the adapter such that the conduit is substantially immovable relative to the canister axis.

In some embodiments, the conduit is substantially immovable relative to the canister axis such that a first end of the conduit is maintained at a substantially same indicia of pressure before and while the apparatus is in use.

In some embodiments, the apparatus is in use when the liquid and an exhaled gas are received in the conduit. In some embodiments, the indicia of the pressure include values in a descending order from a top portion of the canister to a bottom portion of the canister.

In some embodiments, a first end of the conduit is positioned at a value of the indicia of the pressure corresponding to approximately zero cm $H_2O$ pressure. In some embodiments, the conduit is a corrugated tube.

In some embodiments, the adapter has one or more recesses coupling to the second end of the conduit. In some embodiments, the adapter is dimensioned to telescopically couple to the second end of the conduit.

In some embodiments, the apparatus also includes an air filter inlet in one of the lid or the canister and disposed to couple to an air filter. In some embodiments, the air filter is coupled to the air filter inlet. In some embodiments, the air filter inlet is disposed to be left open to the atmosphere. In some embodiments, the air filter inlet may be dimensioned to accept a standard outside diameter of an inline ventilator air filter.

In some embodiments, the apparatus also includes a liquid adjustment subsystem. The liquid level adjustment subsystem includes: a fluid flow mechanism coupleable to a bottom portion of the canister; and a syringe operatively coupleable to the fluid flow mechanism and being disposed to adjust a level of liquid in the canister or provide a volume of the liquid to the canister.

In some embodiments, the apparatus also includes a pressure gauge coupled to one of the lid or the canister. In some embodiments, the pressure gauge is a disposable pressure gauge.

In some embodiments, the pressure gauge may be placed inline for proximal pressure monitoring of the patient. The pressure gauge may connect via standard pressure monitoring tubing to the proximal airway monitoring port of most BNCPAP systems. In some embodiments, the pressure gauge may have an adjustable bleed-off control to adjust the bubble characteristics of the system. The bleed-off control may be simultaneously used to adjust the number of vibrations being generated at a particular flowrate.

In some embodiments, the apparatus also includes a bracket coupled to one of the lid or the canister and disposed to receive a support mechanism. In some embodiments, the bracket is adapted to swivel.

In some embodiments, the support mechanism has an orientation that is substantially perpendicular to the canister axis. In some embodiments, the support mechanism has an orientation that is substantially parallel to the canister axis.

One or more embodiments of the invention is a bubble nasal continuous positive airway pressure system. The system includes a pressure device having a canister, a canister axis and having indicia of pressure on the canister. The pressure device also has a substantially rigid lid and a substantially immovable conduit. The pressure device is disposed to provide a substantially steady pressure while the pressure device is in use. The system also includes an expiratory tube having a first end coupled to the pressure device and having a second end coupled to a first end of a respiratory breathing aid of the system. The system also includes an inspiratory tube having a first end coupled to a gas source of the system and having a second end coupled to a second end of the respiratory breathing aid.

In some embodiments, the pressure device is in use when a liquid and an exhaled gas are received in the conduit.

In one or more embodiments of the present invention, an apparatus for providing pressure into which a patient must exhale is provided. The apparatus includes: a canister having a canister axis and being disposed to hold liquid, the canister having indicia of pressure on the canister, the canister also having a first inlet through the canister; an adapter in the first inlet; and a conduit being retained by the adapter such that the conduit is substantially immovable relative to the canister axis when the apparatus is in use.

BRIEF DESCRIPTION OF THE DRAWINGS

FIG. 4 is an illustration of a BNCPAP system having a pressure device 10 according to one or more embodiments of the present invention.

DETAILED DESCRIPTION OF EMBODIMENTS OF THE INVENTION

Figure 1:
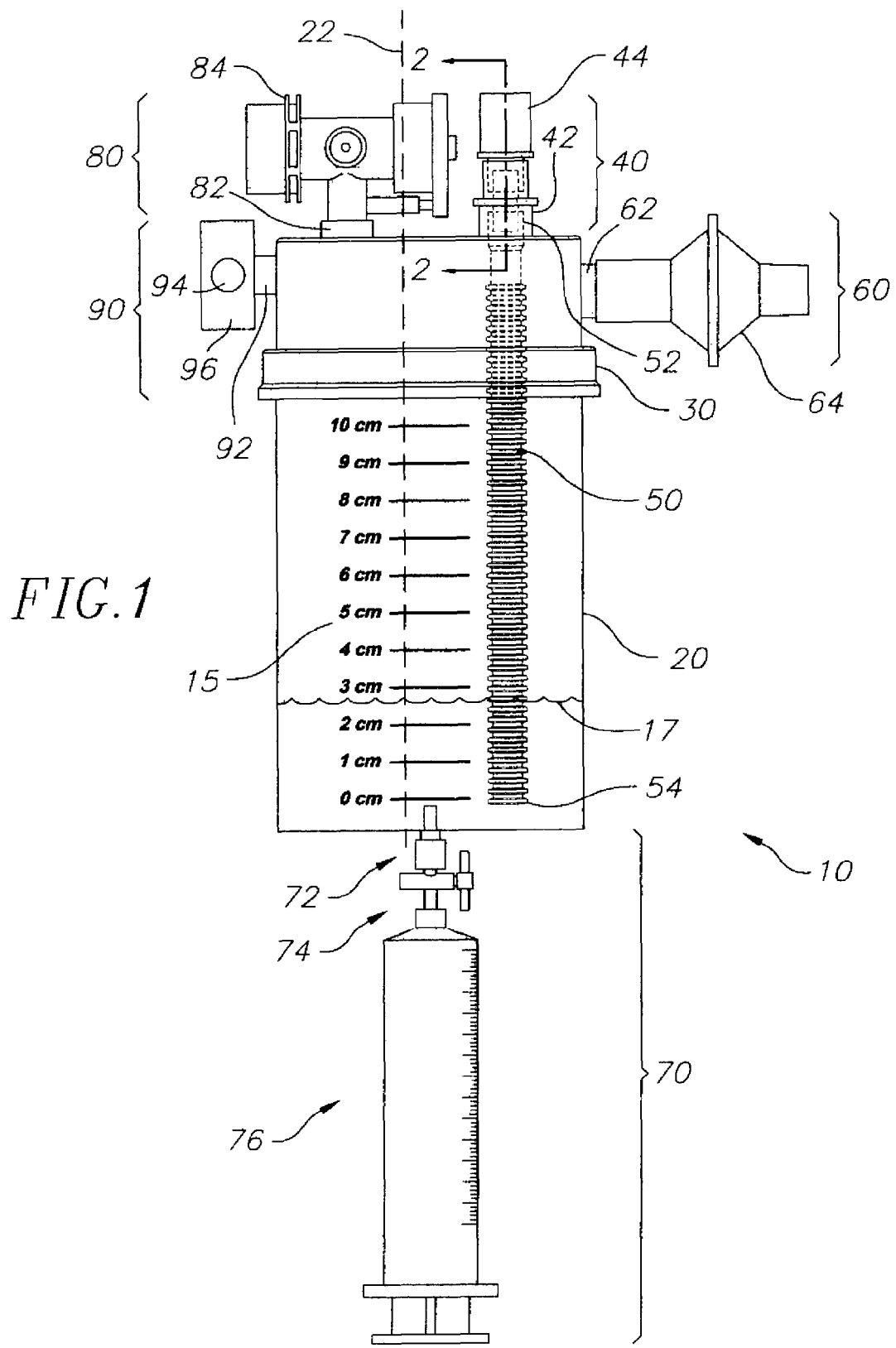
FIG. 1 is a side view of a pressure device according to an embodiment of the present invention.
Figure 2:
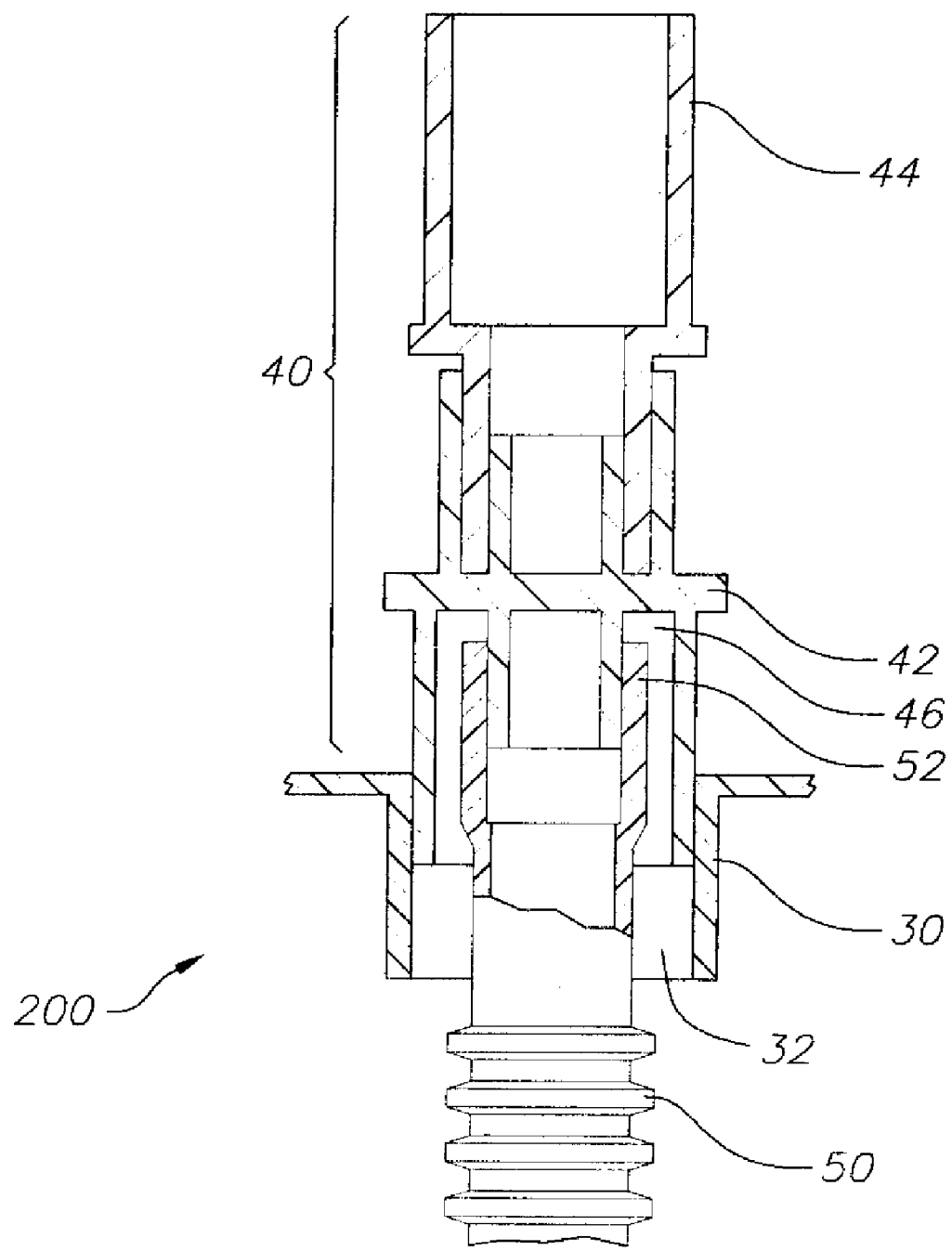
FIG. 2 is an embodiment of a cross-sectional view taken along line 2-2 of the adapter subsystem of the pressure device of FIG. 1.

With reference to FIGS. 1 and 2, the pressure device 10 is disposed to provide pressure into which a patient must exhale. In some embodiments, the pressure device 10 is used by caregivers to provide BNCPAP to infants.

In one embodiment, the pressure device 10 includes a liquid canister 20, a lid 30, an adapter 42 and a substantially immovable conduit 50. In alternate embodiments, the pressure device 10 may also include one or more of the following: an expiratory tube mechanism 44 of an adapter subsystem 40, a filtering subsystem 60, a liquid level adjustment subsystem 70, a pressure measurement subsystem 80 or a structure support subsystem 90.

The liquid canister 20 is formed of a substantially rigid material. The liquid canister 20 has a canister axis 22, which is generally vertical during use of the liquid canister 20 and/or during use of the pressure device in general. The exterior surface of the top portion of the canister 20 may include grooves or may be smooth for receiving a lid 30 over a mouth of the canister 20. The canister 20 is formed of a material allowing a caregiver to view a level of a liquid 17 in the canister 20. The liquid canister 20 is disposed to hold liquid 17. In some embodiments, the liquid 17 is water or acetic acid.

In some embodiments, the liquid 17 may be a solution combining acetic acid and water wherein the solution is approximately 0.25% acetic acid. In some embodiments, the liquid 17 may be vinegar for reducing the growth of common microorganisms known as pseudomonas.

Indicia 15 are permanently or temporarily affixed to the canister 20 through any suitable methods including, but not limited to, being printed in or on the canister 20 or applying to a surface of the canister 20 an indicator strip (not shown) having indicia 15 thereon. The indicia 15 represent the expiratory pressure against which the patient must exhale. The pressure against which a patient must exhale increases as the level of liquid in the canister 20 increases. In some embodiments, the indicia 15 are a plurality of values in descending order from a top portion of the liquid canister 20 to a bottom portion of the liquid canister 20 as shown in FIG. 1. In some embodiments, the lowest value is zero. In some embodiments, the indicia 15 are presented in centimeters and represent centimeters of water pressure, i.e., cm $H_2O$.

Accordingly, in one or more embodiments, a caregiver can conveniently determine the pressure into which a patient must exhale by measuring the height of the liquid 17 in the canister 20 using the indicia 15. In some embodiments, because of the order of the indicia values, the caregiver reduces the need to perform mathematical calculations, such as subtraction, to determine the pressure. The height of the liquid 17 in the canister 20 may be a direct measurement of the exhalatory pressure. During life-threatening emergencies errors in the performance of mathematical calculations can be widespread and dangerous to the patient.

In one embodiment, the diameter of canister 20 is 7.5 cm and the height of the indicia 15 from the top to the bottom portion of the canister 20 is 10 cm. The total height of the canister 20 is between 18 and 22 cm from the bottom of the canister 20 to the height of the pressure gauge in embodiments including pressure gauges. The levels of the liquid 17 are calibrated from 0 to 10 cm corresponding to 0 to 10 cm $H_2O$ exhalatory pressure.

In some embodiments, the canister 20 may also provide a liquid level adjustment subsystem 70 as part of the pressure device 10. The canister 20 may provide the subsystem 70 by having a first inlet (not shown) into which an attachment mechanism 72 of the subsystem 70 is received. The attachment mechanism 72 is disposed to be coupled to fluid flow mechanism 74, which is disposed to stop or reduce the flow of liquid 17 from the canister 20. In some embodiments, the fluid flow mechanism 74 is a stop cock. In some embodiments, the stop cock is a luer-lock stop cock. The luer-lock stop cock connection may be a connection point for a 30 to 60 cm syringe. In some embodiments, syringe 76 is a 30 to 60 cm syringe. Accordingly, the liquid level adjustment subsystem 70 may provide for fairly precise adjustments of the level of the liquid 17 and the exhalatory pressure.

In some embodiments, any suitable mechanism 74 for stopping or reducing the flow of liquid 17 may be used. The fluid flow mechanism is disposed to be coupled to a syringe 76. The syringe 76 is disposed to be operated to drain liquid 17 from the canister 20 or to provide liquid 17 to the canister 20 through methods well-known to those of ordinary skill in the art. Convenient adjustment of the level of liquid in the canister 20 and convenient provisioning of a volume of the liquid into the canister 20 is thereby provided.

The lid 30 is disposed to be coupled to and to substantially cover a mouth portion of the canister 20. Accordingly, the lid 30 may be coupled to the outside of the canister 20 (as shown in FIG. 1) or to the inside of the canister 20 (not shown). The lid 30 may be coupled to the mouth portion of the canister 20 by any suitable method. In some embodiments, ridges on the interior surface of the lid 30 meet with grooves on the surface canister 20 to provide a screw-on pressure device 10. In some embodiments, a smooth interior surface of the lid 30 meets with a smooth surface of the canister 20 and the lid 30 is telescopically coupled to the inside or outside of the canister 20.

The lid 30 is composed of a rigid material. In various embodiments, the rigidity of the lid 30 is such that the lid 30 maintains a substantially same and substantially undeformed shape during insertion of snugly-fitting components into inlets of the lid 30 and during the application of pressure in the pressure device 10. In some embodiments, the lid 30 is composed of hardened plastic, hardened glass or another rigid material. The lid 30 may be any suitable shape for substantially covering a mouth portion of the canister 20.

FIG. 2 is an embodiment of a cross-sectional view 200 taken along line 2-2 of the adapter subsystem of the pressure device of FIG. 1. With reference to FIGS. 1 and 2, the lid 30 includes an adapter inlet 32 through the lid 30. The adapter inlet is dimensioned to snugly receive and retain an adapter 42 of an adapter subsystem 40. The adapter 42 is positioned in the adapter inlet. In some embodiments, the adapter 42 is snugly positioned in the adapter inlet forming a substantially tight seal.

The adapter 42 is disposed to retain a first end 52 of a substantially immovable conduit 50. In some embodiments, the adapter 42 simply receives and retains the first end 52. In some embodiments, the adapter 42 is disposed to retain the conduit 50 such that the conduit 50 is substantially immovable relative to the canister axis 22. In some embodiments, the adapter 42 includes one or more recesses 46 for slidably receiving the first end 52 of the substantially immovable conduit 50. In some embodiments, the adapter 42 is disposed with any suitable structure for snugly receiving and retaining the first end 52 of the substantially immovable conduit 50 in a substantially immovable position. In some embodiments, the adapter subsystem 40 includes an expiratory tube mechanism 44 coupled to the adapter 42. In some embodiments, the expiratory tube mechanism 44 and adapter 42 form a seal that is substantially airtight or only a negligible amount of exhaled gas is released through the seal.

In some embodiments, the expiratory tube mechanism 44 is a 22 millimeter (mm) female adapter connector. Accordingly, the expiratory tube may be coupled to the liquid canister 20 without additional connectors or extensions. Further, the expiratory tube mechanism 44 may couple to the adapter 42. In some embodiments the system also includes an expiratory tube connector (not shown).

Although the embodiment of FIGS. 1, 2 and 4 show the adapter 42 and the expiratory tube mechanism 44 as two separate components, the pressure device may include a single adapter mechanism (not shown) having a first end and a second end wherein the first end is disposed to couple to the conduit 50 and the second end is disposed to couple to the expiratory tube.

The conduit 50 is composed of semi-rigid material. In some embodiments, the conduit 50 is composed of hardened plastic. The conduit 50 is composed of materials such that a second end 54 of the conduit 50 does not substantially move relative to the canister axis when the liquid 17 and an exhaled gas are provided in the conduit 50. In various embodiments, the conduit 50 may be a corrugated tube (as shown in FIG. 1) or a tube having a smooth exterior surface. In some embodiments, the conduit 50 is a non-movable, corrugated tube. In some embodiments, the conduit 50 is immovable and only the level of the liquid 17 determines the exhalatory pressure.

The conduit 50 may be any number of diameters allowing the conduit to be snugly retained by the adapter 42. In some embodiments, the liquid canister 20 may be a canister that can support 10 and 15 mm corrugated conduits. In some embodiments, the conduit 50 may be retained along the interior of the adapter 42 as shown in FIG. 1 or along the exterior of the adapter 42 (not shown).

In various embodiments, the length of the conduit 50 is such that when the adapter 42 is positioned in the adapter inlet 32 and the first end 52 of the conduit 50 is coupled to the adapter 42, a second end 54 of the conduit 50 is aligned with the indicia 15 corresponding to the smallest value in the descending order of indicia 15. In some embodiments, the second end 54 of the conduit 50 is substantially aligned with the indicia 15 corresponding to zero cm $H_2O$ (as shown in FIG. 1).

In various embodiments, the exhalatory pressure is the BNCPAP pressure. In some embodiments, the exhalatory pressure corresponds to the back pressure that is created within the patient's lungs as a result of exhaling into the liquid 17 in the canister 20. The back pressure is proportional to the depth of the conduit 50 below the surface of the liquid 17. This back pressure, which may be measured by the level of the liquid 17, helps open the patient's lungs and assists the patient's breathing. In some embodiments, the conduit 50 is inserted 5 cm into the liquid 17 to generate 5 cm $H_2O$ exhalatory pressure.

In some embodiments, the conduit 50 may be substantially immovable relative to the canister axis 22. In some embodiments, the conduit 50 is substantially immovable relative to the canister axis 22 such that the second end 54 of the conduit 50 is maintained at substantially a same height corresponding to a substantially same value of the indicia 15 before and while the pressure device is in use. The pressure device 10 is in use when the liquid 17 and an exhaled gas is received in the conduit 50. When liquid 17 is placed in the canister 20, and the conduit 50 is placed in the liquid 17, the level of the liquid in the conduit 50 corresponds to the pressure into which a patient must exhale.

In some embodiments, the conduit 50 is substantially immovable relative to the canister axis 22 such that the second end 54 of the conduit 50 is not substantially deflected upward or diagonally upward relative to the canister axis. In some embodiments, the conduit 50 is substantially immovable relative to the canister axis 22 such that the conduit 50 in its entirety does not experience significant displacement along the canister axis during use of the pressure device. In one embodiment, the second end of the conduit 50 is substantially immovable relative to the canister axis such that the second end does not displace more than 1 cm relative to the canister axis. In some embodiments, the bottom of the conduit 50 may be positioned within + or −0.25 cm from the zero cm H20 level.

Referring back to FIG. 1, in some embodiments, the lid 30 may also include a filter inlet (not shown) for providing a filtering subsystem 60 as part of the pressure device 10. The filtering subsystem 60 includes an air filter attachment mechanism 62 disposed to be coupled to the filter inlet and disposed to couple to an air filter 64. In some embodiments, the filter inlet is provided in the canister 20 and the filtering subsystem 60 is provided as part of the pressure device 10 by being coupled to the canister 20.

The attachment mechanism 62 and the air filter 64 each include channels (not shown) formed through the mechanism 62 and the air filter 64. The channels are in communication with one another such that gases associated with the liquid 17 in the canister 20 may travel from the canister 20 through the attachment mechanism 62 and into the air filter 64. In some embodiments, the air filter 64 is composed of material providing filtering of odors.

In some embodiments, the lid 30 may also provide a pressure measurement subsystem 80 as part of the pressure device 10. The lid 30 may provide the subsystem 80 by having a pressure subsystem inlet (not shown) into which the pressure gauge attachment mechanism 82 is received or the subsystem 80 may be coupled to any exterior surface of the lid 30. In some embodiments, the pressure measurement subsystem 80 is coupled to any exterior surface of the canister 20. In some embodiments, the pressure measurement subsystem 80 is free of both the lid 30 and the canister 20. The pressure gauge attachment mechanism 82 is coupled to a pressure gauge 84. In some embodiments, the pressure gauge 84 may be calibrated in cm $H_2O$ pressure. The pressure gauge 84 may be a disposable pressure gauge. In some embodiments, the pressure gauge 84 is a spring-loaded disposable pressure gauge. The pressure gauge 84 may be disposed to measure proximal airway pressure output from and near the respiratory body cavity of the patient. In some embodiments, the respiratory body cavity is the nose or the mouth. The pressure gauge 84 may be discarded after a single patient's use.

In some embodiments, a connector connects a tube from the proximal point of the BNCPAP circuit to the pressure gauge.

With reference to FIGS. 1 and 4, the pressure gauge 84 may be coupled to a proximal airway monitoring conduit 490 that is coupled to expiratory tube 460. In some embodiments, the pressure gauge 84 and the proximal airway monitoring conduit 490 form a seal that is substantially airtight. In some embodiments, the pressure gauge 84 and the proximal airway monitoring conduit 490 form a seal such that only a negligible amount of exhaled gas provided into the conduit 490 is released through the seal. In some embodiments, the pressure gauge 84 and the proximal airway monitoring conduit 490 form a seal such that the amount of any exhaled gas that is released through the seal has a negligible effect on the accuracy of the measurement performed by the pressure gauge 84.

Referring back to FIGS. 1 and 2, in some embodiments, the lid 30 may also provide a structure support subsystem 90 as part of the pressure device 10. The lid 30 may provide the subsystem 90 by having a support subsystem inlet (not shown) into which a structure support subsystem 90 is received or the structure support subsystem 90 may be coupled to any exterior surface of the lid 30. In some embodiments, the subsystem 90 is coupled to any exterior surface of the canister 20.

In some embodiments, the subsystem 90 includes a bracket 96 disposed to couple to a support mechanism (not shown) for mounting the pressure device 10 to the support mechanism. In some embodiments, the bracket 96 is adapted to swivel or otherwise shift in orientation. The bracket 96 may be swiveled to be mounted to a support mechanism having an orientation that is substantially parallel to, substantially perpendicular to or having another orientation relative to the canister axis 22 while maintaining the lid 30 and canister 20 in a substantially upright position.

In some embodiments, the support mechanism is a pole. In some embodiments, the pole has an orientation substantially parallel to the canister axis. In some embodiments, the support mechanism is a rail. In some embodiments, the rail may have an orientation that is substantially perpendicular to the canister axis.

In some embodiments, the subsystem 90 includes a swivel portion 92 coupled to a bracket 96 via a mechanism 94 for coupling the swivel portion 92 to the bracket 96. In some embodiments, the swivel portion 92 is a swivel connector. In some embodiments, the mechanism 94 is a thumb knob bracket mounting screw. In some embodiments, the bracket 96 is a pole-rail mounting bracket.

In some embodiments, the thumb knob bracket mounting screw can be turned and tightened to secure the bracket 96 onto a support mechanism such as a pole or rail. The screw may be used to securely lock the bracket 96 to the support mechanism.

In some embodiments, one or more of the bracket 96, swivel portion 92 or the mechanism 94 is composed of hardened plastic.

Accordingly, in various embodiments, the pressure device 10 may have a built-in mechanism for coupling the pressure device 10 to a range of structures in a patient's room.

In some embodiments, the canister (not shown) having a canister axis may be formed as an apparatus composed of a rigid material and having only a fairly small adapter inlet (not shown) as its mouth portion. Accordingly, the canister may be substantially enclosed on all sides except for the adapter inlet. With reference to FIGS. 1 and 2, the adapter inlet 32 may be sized to snugly receive and retain an adapter 42 disposed to snugly receive and retain the substantially immovable conduit 50. Indicia 15 is provided on the canister in a vertical and descending order from a top portion of the canister to a bottom portion of the canister as described with reference to FIG. 1.

Referring to FIGS. 1 and 2, in some embodiments, the pressure device may include a canister having a canister axis (not shown) and a lid 30. The canister includes an adapter inlet (not shown) positioned at a portion of the canister at a location such that the adapter inlet is above the highest level of liquid to be provided in the canister. For example, the adapter inlet may be near the top side of the exterior surface of the canister. With reference to FIG. 1, the adapter inlet is dimensioned to snugly receive and retain an adapter 42. The adapter 42 is disposed to snugly receive a conduit (not shown) that is substantially immovable relative to the canister axis when the apparatus is in use. In some embodiments, the substantially immovable conduit may be any suitable shape such that the conduit is substantially vertical over the portion of the canister in which liquid 17 is provided and such that the bottom of the conduit is substantially at a level of liquid corresponding to zero cm $H_2O$. In some embodiments, the conduit is an L-shaped conduit having a substantially vertical portion of the L-shape provided over the portion of the canister in which liquid 17 is provided. Indicia 15 is provided on the canister in a vertical and descending order from a top portion of the canister to the bottom portion of the canister.

In some embodiments, the pressure device may be a single device having a canister that includes a canister portion and a lid portion integrally formed as a single unit. The canister portion may include indicia on the canister portion. The pressure device may also have one or more of any of the components and/or subsystems shown in FIG. 1. One or more of the components and/or subsystems may be integrally formed in the pressure device.

Figure 3:
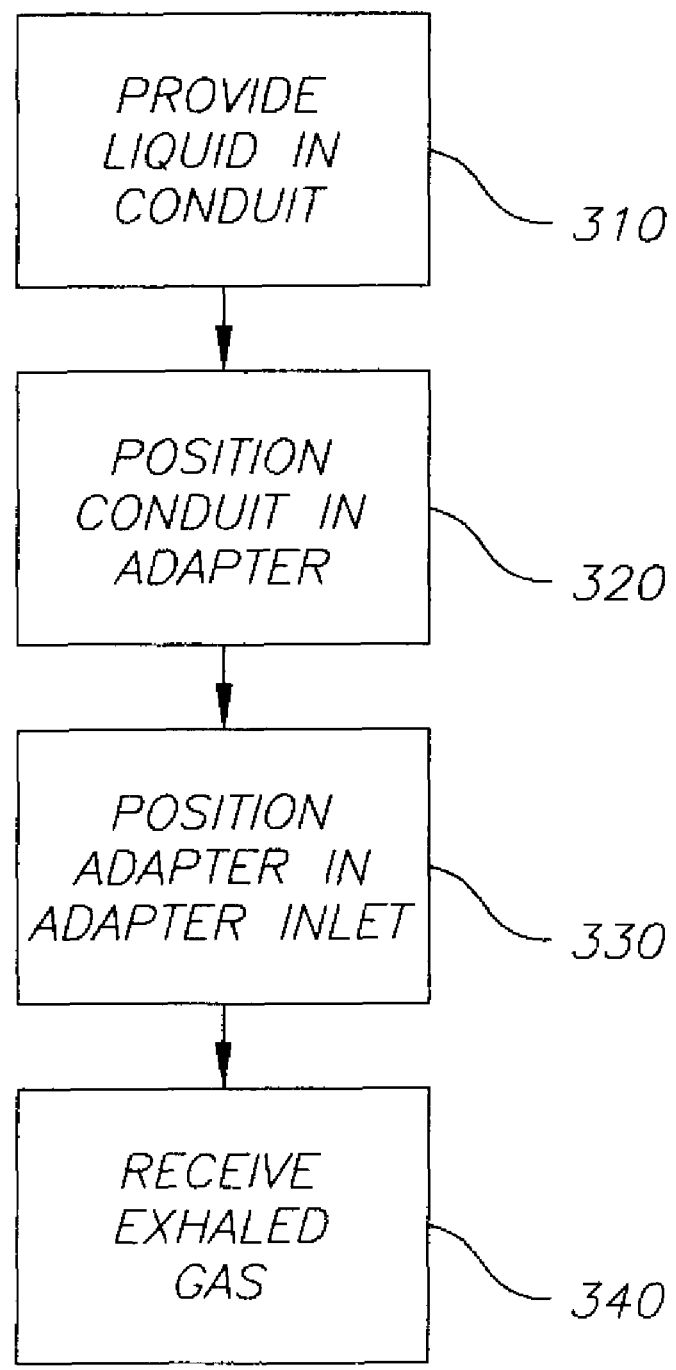
FIG. 3 is a flowchart of a method of operating one or more embodiments of the pressure device of the present invention.

FIG. 3 is a flowchart of a method of operating one or more embodiments of the pressure device of the present invention. Liquid is provided or adjusted 310 in the conduit. The immovable conduit is snugly positioned 320 in the adapter. The adapter is positioned 330 in the adapter inlet. In some embodiments, exhaled gas is received 340 in the conduit.

In some embodiments, the method also includes one or more of the following steps. Gases associated with the liquid in the canister are filtered. Proximal pressure near the respiratory body cavity of a patient is measured. The pressure device is mounted.

FIG. 4 is an illustration of a BNCPAP system having a pressure device 470 according to one or more embodiments of the present invention. The pressure device 470 may be any of the aforementioned embodiments of pressure devices or combination thereof.

The system includes a gas source 410 coupled to a humidifier 420, which is coupled to an inspiratory tube 430, which is coupled to a thermometer 440, which is coupled to a respiratory breathing aid 450, which is coupled to an expiratory tube 460, which is coupled to a pressure device 470. In some embodiments, the system also includes a thermometer 480, a proximal airway monitoring conduit 490 and a pressure gauge 495.

In some embodiments, the gas source 410 includes one or more of an oxygen flowmeter or a gas blender. The oxygen flowmeter may provide gas at rates above 5-6 liter per minute (1 pm), which can result in back pressure and the total pressure to the patient exceeding the pressure indicated by the level of the liquid 17 in the canister 20. Accordingly, measurement of proximal airway pressure may be used to verify that the level of the liquid 17 correctly indicates the level of exhalatory pressure delivered to the patient.

In some embodiments, the respiratory breathing aid 450 includes one or more of nasal prongs, a face mask or a mechanism disposed to be inserted into a patient's mouth. In some embodiments, the nasal prongs are inserted less than one inch into the patient's nose.

In some embodiments, the system includes a pressure device having a canister with a canister axis and indicia of pressure on the canister. The pressure device also has a substantially rigid lid and a substantially immovable conduit in the pressure device. The pressure device is disposed to provide a substantially steady pressure while the pressure device is in use. The system also includes an expiratory tube having a first end coupled to the pressure device and having a second end coupled to a first end of a respiratory breathing aid of the system. The system also includes an inspiratory tube having a first end coupled to a gas source of the system and having a second end coupled to a second end of the respiratory breathing aid. In some embodiments, the pressure device is in use when the liquid and an exhaled gas are received in the conduit.

The system components may be any of the aforementioned embodiments of or combinations thereof.

In some embodiments, with reference to FIG. 1, a combination expiratory tube and conduit (not shown) is coupled to the respiratory breathing aid is provided through an expiratory tube adapter (not shown) and into the liquid 17 of the canister 20. The combination expiratory tube and conduit may be provided through the expiratory tube adapter such that the combination expiratory tube and conduit is substantially immovable while the pressure device is in use. The pressure device is in use when a volume of the liquid 17 is provided in the portion of the combination expiratory tube and conduit and the combination expiratory tube and conduit receives exhaled gas.

While embodiments of the present invention have been described in connection with exemplary embodiments, it is to be understood that the invention is not limited to the disclosed embodiments, but, on the contrary, is intended to cover various modifications and equivalent arrangements included within the spirit and scope of the specification, appended claims and their equivalents.

What is claimed is:

1. An apparatus, comprising:
    a canister having a canister axis and being disposed to hold liquid, the canister having indicia of pressure on the canister;
    a substantially rigid lid disposed to substantially cover a mouth of the canister and having a first inlet through the lid;
    an adapter in the first inlet;
    a conduit fixed to the first end of the adapter such that the conduit is substantially immovable relative to the canister axis;
    a connector having a first end coupled to a second end of the adapter, wherein the connector and the second end of the adapter are coupled such that a channel is formed between the conduit and the connector; and
    a liquid adjustment subsystem, the liquid level adjustment subsystem comprising: a fluid flow mechanism coupleable to a bottom portion of the canister; and a syringe operatively coupleable to the fluid flow mechanism and being disposed to at least one of adjust a level of liquid in the canister or provide a volume of the liquid to the canister.

2. The apparatus of claim 1, wherein the conduit is substantially immovable relative to the canister axis such that a first end of the conduit is maintained at a substantially same indicia of pressure before and while the apparatus is in use.

3. The apparatus of claim 1, wherein the apparatus is in use when an exhaled gas is received in the conduit.

4. The apparatus of claim 1, wherein the indicia of the pressure comprises values in a descending order from a top portion of the canister to a bottom portion of the canister, wherein the top portion of the canister corresponds to a portion of the canister proximate to the mouth of the canister.

5. The apparatus of claim 1, wherein the first end of the conduit is positioned at a value of the indicia of the pressure corresponding to approximately zero cm $H_2O$ pressure.

6. The apparatus of claim 1, wherein a second end of the conduit is fixed within one or more recesses proximate to the first end of the adapter.

7. The apparatus of claim 1, wherein a second end of the conduit is telescopically fixed to the first end of the adapter.

8. The apparatus of claim 1, further comprising an air filter inlet disposed to couple to an air filter and located in at least one of the lid or the canister.

9. The apparatus of claim 8, further comprising the air filter coupled in the air filter inlet.

10. The apparatus of claim 1, further comprising a pressure gauge coupled to at least one of the lid or the canister.

11. The apparatus of claim 10, wherein the pressure gauge is a disposable pressure gauge.

12. The apparatus of claim 1, further comprising a bracket disposed to receive a support mechanism and coupled to at least one of the lid or the canister.

13. The apparatus of claim 12, wherein the bracket is adapted to swivel.

14. The apparatus of claim 12, wherein the support mechanism has an orientation that is substantially perpendicular to the canister axis.

15. The apparatus of claim 12, wherein the support mechanism has an orientation that is substantially parallel to the canister axis.

16. The apparatus of claim 1, wherein the connector is telescopically coupled to the adapter.

17. The apparatus of claim 1, wherein the apparatus is a bubble nasal continuous positive airway pressure apparatus.

18. A bubble nasal continuous positive airway pressure system
- a canister having a canister axis and being disposed to hold liquid, the canister having indicia of pressure on the canister, the canister also having a first inlet through the canister;
- an adapter in the first inlet;
- a conduit being fixed to a first end of the adapter such that the conduit is substantially immovable relative to the canister axis;
- a connector having a first end coupled to a second end of the adapter, wherein the connector and the second end of the adapter are coupled such that a channel is formed between the conduit and the connector; and
- a liquid adjustment subsystem, the liquid level adjustment subsystem comprising: a fluid flow mechanism coupleable to a bottom portion of the canister; and a syringe operatively coupleable to the fluid flow mechanism and being disposed to at least one of adjust a level of liquid in the canister or provide a volume of the liquid to the canister;
- an expiratory tube having a first end coupled to the pressure device and having a second end coupled to a first end of a respiratory breathing aid of the system; and an inspiratory tube having a first end coupled to a gas source of the system and having a second end coupled to a second end of the respiratory breathing aid.

19. The system of claim 18, wherein the pressure device is in use when an exhaled gas is received in the conduit.

20. An apparatus comprising:
- a canister having a canister axis and being disposed to hold liquid, the canister having
- indicia of pressure on the canister, the canister also having a first inlet through the canister;
- an adapter in the first inlet; and
- a conduit being fixed to a first end of the adapter such that the conduit is substantially immovable relative to the canister axis;
- a connector having a first end coupled to a second end of the adapter, wherein the connector and the second end of the adapter are coupled such that a channel is formed between the conduit and the connector; and
- a liquid adjustment subsystem, the liquid level adjustment subsystem comprising: a fluid flow mechanism coupleable to a bottom portion of the canister; and a syringe operatively coupleable to the fluid flow mechanism and being disposed to at least one of adjust a level of liquid in the canister or provide a volume of the liquid to the canister.

* * * * *